United States Patent [19]

Jacobsen et al.

[11] 4,180,068

[45] Dec. 25, 1979

[54] BI-DIRECTIONAL FLOW CATHETER WITH RETRACTABLE TROCAR/VALVE STRUCTURE

[75] Inventors: Stephen C. Jacobsen; Robert L. Stephen; Peter Hansen, all of Salt Lake City, Utah

[73] Assignee: Motion Control, Incorporated, Salt Lake City, Utah

[21] Appl. No.: 895,858

[22] Filed: Apr. 13, 1978

[51] Int. Cl.² ................ A61M 5/00; A61B 17/34
[52] U.S. Cl. .................... 128/214 R; 128/221; 128/347; 128/DIG. 16; 128/214.4
[58] Field of Search ............ 128/214 R, 214.4, 221, 128/347–351, DIG. 16

[56] References Cited

U.S. PATENT DOCUMENTS

| 1,845,727 | 2/1932 | Slaughter | 128/347 X |
| 3,081,770 | 3/1963 | Hunter | 128/221 |
| 4,073,297 | 2/1978 | Kopp | 128/214.4 |
| 4,098,275 | 7/1978 | Consalvo | 128/221 X |

FOREIGN PATENT DOCUMENTS

| 496458 | 7/1950 | Belgium | 128/347 |
| 716726 | 10/1931 | France | 128/347 |

*Primary Examiner*—Dalton L. Truluck
*Attorney, Agent, or Firm*—Criddle, Thorpe & Western

[57] ABSTRACT

A bi-directional flow catheter for insertion into the body of a patient for the simultaneous introduction into and withdrawal therefrom of fluid. The catheter includes a primary tube having open distal and proximal ends, and a pair of branching tubes, each of which branch from a different side of the primary tube. The primary tube also has an opening in one side thereof to allow introduction of fluid. An elongate trocar/valve member is disposed in the primary tube and is movable longitudinally therein between an insert position and a flow position. One end of the trocar/valve member tapers to a cutting edge which protrudes from the opening in the distal end of the primary tube when the member is in the insert position. The trocar/valve member is formed to prevent communication between the side opening and the opening in the distal end of the primary tube, and to cover the passageways between the primary tube and respective ones of the branching tubes when the member is in the insert position. When the member is in the flow position, the cutting end thereof is withdrawn from the distal opening and communication is allowed between the side opening and one of the branching tubes and between the distal opening and the other of the branching tubes to thereby allow simultaneous introduction of fluid into and withdrawal of fluid from the body of a patient.

11 Claims, 8 Drawing Figures

BI-DIRECTIONAL FLOW CATHETER WITH RETRACTABLE TROCAR/VALVE STRUCTURE

BACKGROUND OF THE INVENTION

This invention relates to a catheter and trocar structure which enables simultaneous, bi-directional flow of fluids therethrough.

There exists a variety of catheter designs for use in injection or withdrawal of fluids from body cavities, ducts, vessels, or the like. Examples of some catheter or similar tubular designs are shown in U.S. Pat. Nos. 2,393,002, 3,459,189, 3,833,033 and 3,929,126. Typically, the catheters include a stylet or trocar inserted within the catheter to facilitate puncturing the body cavity, duct or vessel, and to provide support for the catheter. Once the catheter has been inserted into the body, the stylet or trocar is withdrawn to then allow either injection or withdrawal of fluid through the catheter.

In many treatment situations, it is desirable to introduce fluid into and withdraw fluid from the body simultaneously. One such situation is the withdrawal of blood from a blood vessel for treatment by an artificial kidney and then the reintroduction of the treated blood back into the blood vessel. In the typical manner of simultaneous withdrawal from and introduction of fluid into a body, two separate needles or catheters are utilized and this means two separate punctures must be made with the attendant discomfort, possibility for infection, damage to blood vessels, and trauma.

Single needle catheters have been suggested but the operation of such catheters, in most instances, is a type of ping-pong flow where fluid is alternately introduced into and withdrawn from the body. The disadvantage of this is that some of the fluid which may have just been introduced into the body may also almost immediately be withdrawn. This occurs because the entrance and exit for the needle in the body are at the same location. Also, higher flow speeds or quantities are required for the alternate introduction and withdrawal of fluid to achieve the same average rate of flow as could be achieved with a simultaneous introduction and withdrawal operation.

One catheter structure which has been proposed involves the use of concentric tubes in which an inner tube is used for introducing fluid into a body and the outer tube is used for withdrawing fluid from the body, or vice versa. One implementation of this arrangement is to first place a removable cutting tocar within the outer tube to facilitate insertion of the catheter into the body. Then, after insertion, the trocar is removed and the smaller inner tube is placed within the outer tube to enable introduction and withdrawal of fluid from the body. This implementation is cumbersome and time consuming, which necessarily increases the discomfort of the patient, and vulnerable to infection. Also, because of the concentricity of the two tubes, the passages through which the fluid flows, at least the passage between the larger tube and the smaller inner tube, present a significant flow resistance because of the low hydraulic radius. This increases the shear levels which, for blood withdrawal, causes greater damage to the blood.

It is generally desirable that while a catheter is being inserted into the body of a patient that fluid be prevented from flowing into the catheter. The single needle catheter, and concentric catheters generally make no provision for preventing such flow during insertion.

SUMMARY OF THE INVENTION

It is an object of the present invention to provide a single-tube double-lumen catheter through which fluids may be simultaneously introduced into and withdrawn from the body of a patient.

It is another object of the present invention to provide such a catheter which may be easily inserted into the body of a patient without causing significant damage to the skin or subcutaneous fascia.

It is still another object of the present invention, in accordance with one aspect thereof, to provide such a catheter in which fluid is prevented from flowing into the catheter during insertion into the body of a patient.

It is a further object of the present invention, in accordance with another aspect thereof, to provide such a catheter in which the two lumens have fairly high hydraulic radii to thereby reduce flow resistance of fluids traveling therethrough.

It is an additional object of the present invention to provide such a catheter which is simple in construction and easy to use.

These and other objects of the present invention are realized in one illustrative embodiment thereof which includes a primary tube having open forward and rearward ends and an opening in one side thereof. A duct means is provided near the rearward end of the primary tube to enable communication with the interior of the primary tube. An elongate trocar/valve member is disposed in the primary tube and is movable longitudinally therein between an insert position and a flow position. The trocar/valve member includes a tapered end which protrudes through the forward opening of the primary tube when the member is in the insert position and which is retracted into the primary tube when the member is in the flow position. The trocar/valve member includes occluding structure which prevents communication between the side opening and the forward opening in the primary tube regardless of which position the member is in. The trocar/valve member also includes a first passage defining structure which enables communication between the side opening in the primary tube and the duct means when the member is in the flow position. Second passage defining structure enables communication between the forward opening in the primary tube and a point located near the rearward end of the tube. In one embodiment of the invention the second passage defining structure defines a passage from the forward opening of the primary tube to a side opening in the primary tube located near the rearward end thereof. In another embodiment, the second passage defining structure defines a passage through the trocar/valve member from one end thereof to the other end.

BRIEF DESCRIPTION OF THE DRAWINGS

The above and other objects, features and advantages of the present invention will become apparent from the following detailed description presented in connection with the accompanying drawing in which.

DETAILED DESCRIPTION

Figure 1:
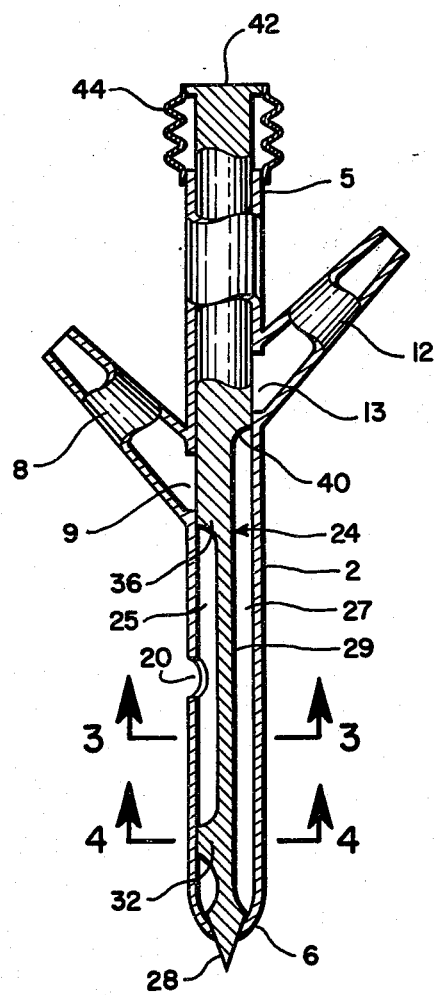
FIG. 1 is a cross-sectional view of one illustrative embodiment of the present invention in which a trocar/valve member is in an insert position.

Referring to FIGS. 1 through 4 of the drawings, there is shown one illustrative embodiment of the present invention which provides an elongate, generally cylindrical primary tube 2 having an open rearward or proximal end 5 and an open forward or distal end 6. The interior and exterior diameters of the primary tube 2 are generally uniform except at the distal end 6 in which case the interior and exterior surfaces thereof generally taper inward, as shown, to form a truncated conically-shaped termination.

Branching from each side of the primary tube 2 are a pair of tubes 8 and 12. The tubes 8 and 12 communicate with the interior of the primary tube 4 through the respective openings 9 and 13 on opposite sides of the primary tube. The tubes 8 and 12 may be joined to the primary tube 2 in any standard fashion and at various locations along, but generally on opposite sides of, the primary tube.

Located between the branching tube 8 and the distal end 6 of the primary tube 2, is an opening 20 in the wall of the primary tube. As will be discussed more fully later, this opening 20 is provided to allow fluid to flow thereinto from the body of a patient to thereby withdraw or drain fluid from the patient.

Figure 2:
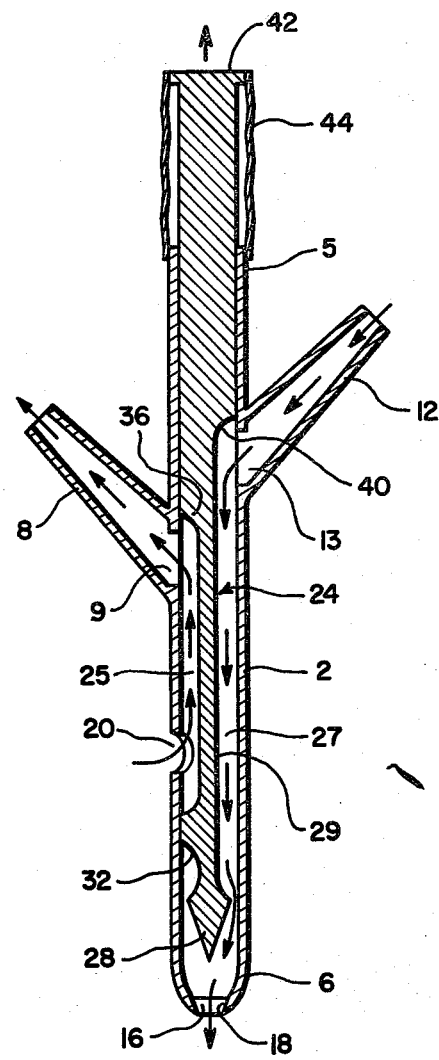
FIG. 2 is a cross-sectional view of the embodiment of FIG. 1 with the trocar/valve member shown in the flow position.
Figure 3:
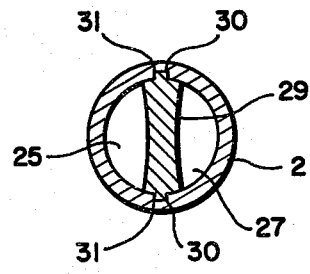
FIG. 3 is a cross-sectional view of the embodiment of FIG. 1 taken along lines 3—3.

Disposed within the primary tube 2 is en elongate trocar/valve member 24 which is slidable longitudinally in the interior of the tube 2 between an insert position shown in FIG. 1 and a flow position shown in FIG. 2. The trocar/valve member 24 is dimensioned to fit snuggly within the tube 2 to slidingly contact the interior walls of the primary tube at all contiguous surface areas except where certain cut-away portions are provided in the member 24. One end 28 of the trocar/valve member tapers to a sharp point suitable for piercing a person's skin. This tapered end is generally conical in shape and is dimensioned so that a portion thereof will protrude through an opening 16 in the distal end 6 of the primary tube 2 when the trocar/valve member 24 is in the insert position (FIG. 1). The inside surface of the lip 18 of the distal opening 16 is beveled to conform and sealingly mate with the tapered surface of the trocar/valve member end 28 when the member is in the insert position. Thus, when in the insert position, the exterior surface of the distal end 6 of the primary tube 2 and of the tapered end 28 of the member 2 present a generally smooth continuous exterior conical surface to facilitate insertion of the distal end of the tube 2 into the body of a patient.

The trocar/valve member 24 is constructed to divide the interior of the primary tube 2 into two sections or lumens 25 and 27. This is done by providing cut-away portions on either side of the member 24, in a central part thereof, to form a dividing, generally I-shaped, beam 29 which extends between the top and bottom wall of the tube 2 (see FIG. 3). Grooves or slots 30 are formed in the top and bottom wall of the tube 2 to provide a guide for the sliding movement of the trocar/valve member 24. Raised rails 31 are formed on the top and bottom of the member 24 to extend substantially the length of the member. The rails 31 are slidingly fitted into corresponding slots 30 to prevent rotation of the member 24 within the primary tube 2.

Figure 4:
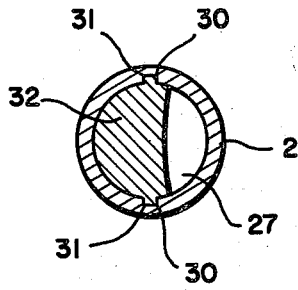
FIG. 4 is a cross-sectional view of the embodiment of FIG. 1 taken along lines 4—4.

Located rearwardly of the tapered end 28 of the trocar/valve member 24 is an occluding, enlarged portion 32 having a generally semi-circular cross-section (FIG. 4). The enlarged portion 32 sealingly contacts the top, bottom and one side interior wall of the tube 2 as shown in FIG. 4 to prevent communication between the distal opening 16 and the side opening 20 in the tube.

Located rearwardly of and on the same side of the trocar/valve member 24 as the enlargement 32 is a second enlarged portion 36, also having a generally semi-circular cross section. When the trocar/valve member 24 is in the insert position of FIG. 1, the enlarged portion 36 covers the opening 9 between the tube 8 and the interior of the primary tube 2. Thus, in the insert position, no fluid can flow from the lumen 25 to the tube 8 which, of course, is what is desired during insertion of the catheter into the body of the patient. The two enlarged portions 32 and 36 define in the trocar/valve member 24 a passage or cut-away section between the two portions through which fluid may flow from the opening 20 to the tube 8 (as indicated by the arrows in FIG. 2) when the member 24 is in the flow position. In this position, the trocar/valve member 24 is pulled rearwardly so that the enlarged portion 36 does not cover the opening 9 and thus the fluid can flow therethrough.

A third enlarged portion 40 is located rearwardly of the enlarged portion 36, but on the other side of the trocar/valve member 24. The trocar/valve member 24 at this location is circular in cross section to substantially fill the interior space of the primary tube 2. When the member 24 is in the insert position (FIG. 2), the enlarged portion 40 covers the opening 13 to prevent communication between the lumen 27 and the tube 12. When the member 24 is in the flow position (FIG. 2), the enlarged portion 40 is withdrawn from over the opening 13 so that fluid can flow from the tube 12 through the opening 13 to the lumen 27 and then out the distal opening 16 of the primary tube 2, as indicated by the arrows in FIG. 2.

Rearwardly of the enlarged portion 40, the trocar/valve member 24 can take various shapes but is shown in the drawings as being generally cylindrical to fill the space in the proximal end of the primary tube 2. The rear end 42 of the trocar/valve member 24 protrudes from the primary tube 2 to enable sliding the member within the tube. Flexible tubing or bellows 44 is connected between the end 42 of the trocar/valve member 24 and the proximal ends of the tube 2 to seal off the interior of the tube. Such connections may be made in any suitable fashion such as with adhesives, clamps, etc., the purpose being to prevent the leaking of fluid out the proximal end of the tube 2 onto the person using the catheter.

In use, a source of fluid to be introduced into the body of a patient would be connected to tube 12 and a fluid sink would be connected to tube 8 to receive fluid withdrawn from the patient. Of course, appropriate pumping apparatus could be utilized in conjunction with such a source and sink if pumping of the fluid were desired. Also, the source of fluid could be connected to tube 8 and the fluid sink connected to tube 12 so that the flow of fluids indicated by the arrows in FIG. 2 would be reversed. For introduction and withdrawal of fluid from the body of a patient, the trocar/valve member would be moved to the insert position shown in FIG. 1, and the catheter then inserted into the body of the patient. The member 24 would then be pulled rearwardly to the flow position of FIG. 2 to allow fluid to be injected into and withdrawn from the body simultaneously. Fluid would be supplied from a fluid source through tube 12 to flow through lumen 27 and out the opening 16 of the tube 2. Fluid would be withdrawn from the body by flowing through opening 20, through lumen 25 and out the tube 8 to a fluid sink. Enlarged portions 36 and 40 act as valves to prevent fluid from flowing rearwardly in the tube 2, and enlarged portion 32 similarly acts as a valve to prevent fluid from flowing between the distal opening 16 and side opening 20.

In the manner described, a single-tube, double-lumen catheter is provided by which fluids may be simultaneously introduced into and withdrawn from the body of a patient. The cross sections of the lumens are generally semi-circular to present fairly high hydraulic radii which reduces flow resistance and shear levels. This is especially advantageous for blood introduction or withdrawal since damage to blood is minimized. The catheter is simple in construction and yet enables a bi-directional flow of fluid therein.

Figure 5:
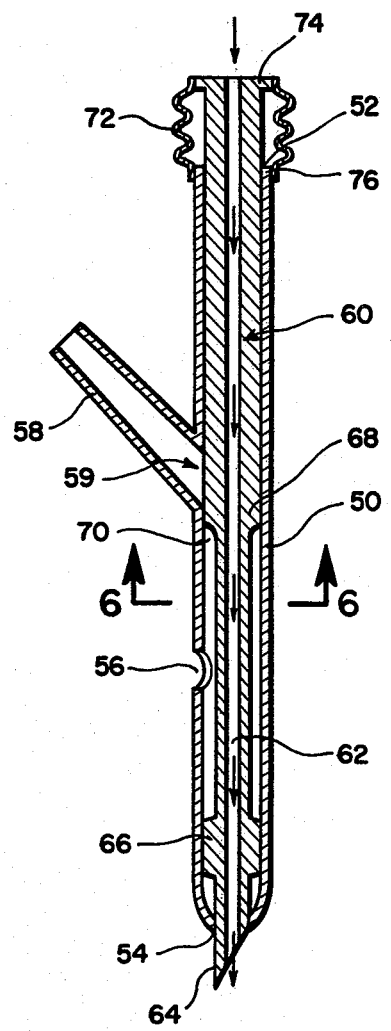
FIG. 5 is a cross-sectional view of another embodiment of the present invention.
Figure 6:
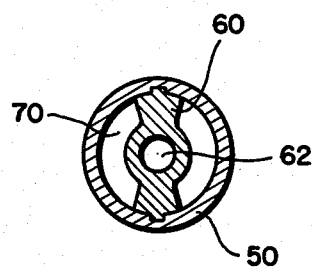
FIG. 6 is a cross-sectional view of the embodiment of FIG. 5 taken along lines 6—6.

FIGS. 5 and 6 shows an alternative embodiment of the invention. In this embodiment, a primary tube 50 is again provided, with an open rearward end 52 and a tapered open forward end 54. The primary tube 50 also has an opening 56 located in one side thereof and a branching tube 58 located on the same side but rearwardly of the opening 56. The branching tube 58 and the opening 56 both enable communication with the interior of the primary tube 50.

Disposed within the primary tube 50 is an alongate trocar/valve member 60 which is slidable longitudinally in the interior of the tube 50 again between an insert position (shown in FIG. 5) in which one end of the member 60 protrudes through the opening 54 of the primary tube 50, and a flow position in which the member 60 is withdrawn into the primary tube. Formed axially with the trocar/valve member 60 is a bore 62 which extends the full length of the member 60. One end 64 of the trocar/valve member 60 is tapered as shown to enable piercing a person's skin.

Located just rearwardly of the tapered end 64 of the trocar/valve member 60 is an occluding enlargement 66 formed in the member 60. This enlargement sealingly contacts the interior walls of the primary tube 50 to prevent communication between the forward opening 54 and the side opening 56. Another enlargement 68 is formed in the trocar/valve member 60 to cover an opening 59 leading to the branching tube 58 when the member 60 is in the insert position. The enlargement 68 acts as a valve to prevent the flow of fluid between the branching tube 58 and the interior of the primary tube 50.

As with the earlier described embodiment of FIGS. 1–4, the enlargements 66 and 68 of the embodiment of FIG. 5 also serve to define in the trocar/valve member 60 a passage or cut-away section 70 through which fluid can flow between the opening 56 and the branching tube 58 when the member 60 is in the flow position. When in the flow position, the trocar/valve member 60 is pulled rearwardly so that the enlargement 68 does not cover the opening 59.

A bellows 72 connects and encloses a rear end 74 of the trocar/valve member 60 and a rear end 76 of the primary tube 50 to seal off the interior of the tube 50 in a manner similar to that described for the embodiment shown in FIGS. 1–4.

The use of the catheter of FIG. 5 is similar to the use of the earlier described embodiment except that fluid is applied to the body of a person through the bore 62 of the trocar/valve member 60 (or withdrawn from the body). With the catheter of FIG. 5, fluid may be applied through the bore 62 when the trocar/valve member 60 is in either the insert or flow position. Of course, bi-directional flow is possible when the member 60 is in the flow position.

Figure 7:
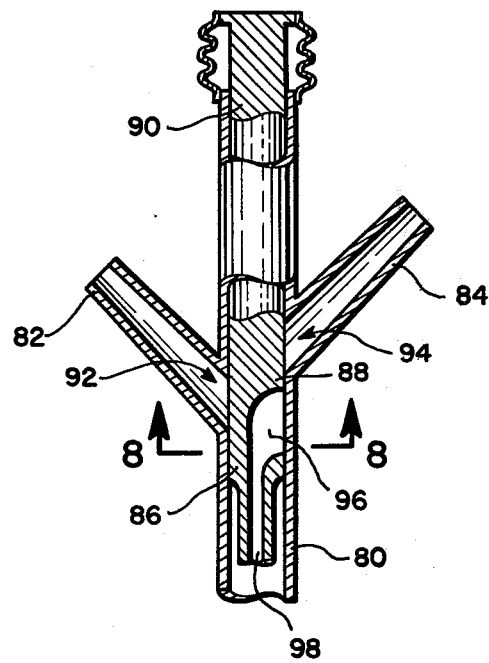
FIG. 7 is a fragmented, cross-sectional view of still another embodiment of the present invention.
Figure 8:
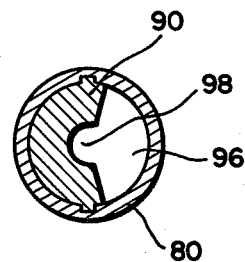
FIG. 8 is a cross-sectional view of the embodiment of FIG. 7 taken along lines 8—8.

Shown in FIGS. 7 and 8 is still another embodiment of the present invention. This embodiment is the same structurally at its forward end as is the embodiment of FIGS. 5 and 6 and so the forward end is not shown. At the rearward end, two branching tubes 82 and 84 branch from each side of a primary tube 80. Enlargements 86 and 88 are formed on each side of a trocar/valve member 90 to cover openings 92 and 94 respectively when the member 90 is in the previously described insert position. When the trocar/valve member 90 is pulled rearwardly to a flow position so that the enlargements 86 and 88 are removed from covering the openings 92 and 94, a bi-directional flow of fluid in the catheter may take place. One direction of flow is between the branching tube 82 and a side opening (not shown) as with the other embodiments. The other direction of flow is from the branching tube 84 through a side cavity 96 formed in the trocar/valve member 90 to a bore 98 also formed in the member 90 to extend from the cavity 96 axially to the forward end of the member 90. Thus, the catheter embodiment of FIGS. 7 and 8 is similar to the embodiment of FIGS. 1–4 in that both include a pair of branching tubes, but in the FIGS. 7 and 8 embodiment, one of the branching tubes communicates with a bore located centrally in the trocar/valve member 90—at least when the member 90 is in the flow position—whereas in the FIGS. 1–4 embodiment, the branching tubes communicate with respective lumens formed on each side of the trocar/valve member.

It is to be understood that the above-described structure is only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:
1. A bi-directional flow catheter comprising
an elongate primary tube having open rearward and forward ends, a side opening in one side thereof, and duct means located rearwardly of said side opening for enabling communication with the interior of the primary tube, and
a trocar/valve member disposed in and slidable longitudinally within said primary tube between an insert position and a flow position, said member comprising
an elongate body, one end of which is tapered, said tapered end protruding from the open forward end of the primary tube when the trocar/valve member is in the insert position to facilitate puncture of tissue into which the catheter is inserted, occluding means for preventing communication between the open forward end of the primary tube and said side opening, first passage defining means for enabling communication between said side opening and said duct means when the trocar/valve member is in the flow position, and second passage defining means for enabling communication between the open forward end of the primary tube and a point located at the rearward end of said primary tube.

2. A catheter as in claim 1 wherein said duct means comprises a first tubular member branching from one side of said primary tube and an opening in the primary tube leading to the tubular member, wherein said occluding means comprises a first enlargement formed on one side of said elongate body near the tapered end to contact the interior walls of said primary tube and prevent communication between the forward open end of the primary tube and said side opening, and wherein said first passage defining means comprises a second enlargement formed on said one side of said elongate body and spaced rearwardly from said first enlargement to form a passage therebetween for conducting fluid between said side opening and said first tubular member when the trocar/valve member is in the flow position, said second enlargement being disposed to cover the opening to said first tubular member when the trocar/valve member is in the insert position.

3. A catheter as in claim 2 further comprising a second tubular member branching from the other side of said primary tube at said point located at the rearward end of the primary tube, and an opening in the primary tube leading to said second tubular member, and wherein said second passage defining means comprises a third enlargement formed on the other side of said elongate body to cover the opening to said second tubular member when the trocar/valve member is in the insert position, and to expose the opening when the trocar/valve member is in the flow position so that fluid may flow between the second tubular member and the open foward end of said primary tube.

4. A catheter as in claim 2 wherein said second passage defining means comprises a bore formed axially in said elongate body to extend the full length thereof.

5. A catheter as in claim 2 further comprising a second tubular member branching from the other side of said primary tube at said point located at the rearward end of the primary tube, and an opening in the primary tube leading to said second tubular member, and wherein said second passage defining means comprises
a cavity formed in the other side of said elongate body to be contiguous to the opening to said second tubular member when the trocar/valve member is in the flow position, and
a bore formed axially in said elongate body to extend from said cavity to the tapered end of the elongate body.

6. A bi-directional flow catheter comprising
(a) an elongate primary tube having open distal and proximal ends and an opening in one side thereof,
(b) a first tube branching from said one side of the primary tube at a location between said side opening and the proximal end of the primary tube to enable communication with the interior of the primary tube, (c) a second tube branching from the other side of said primary tube to communicate with the interior thereof, and (d) a trocar/valve member disposed in and slidable longitudinally within said primary tube between an insert position and a flow position, said trocar/valve member having an elongate body with
a tapered tip at one end thereof,
a first enlarged portion formed on one side of the body for preventing communication between the open distal end of the primary tube and said opening,
a second enlarged portion formed on said one side of the body and spaced from the first enlarged portion to form a valley therebetween, and
a third enlarged portion formed on the other side of the body, (e) said trocar/valve member being positioned, when in the insert position, so that
the tapered end of the member protrudes through the open distal end of said primary tube,
the second enlarged portion is positioned adjacent said first branching tube to prevent communication between said side opening and the first branching tube, and
the third enlarged portion is positioned adjacent said second branching tube to prevent communication between the open distal end of the primary tube and the second branching tube, and (f) said trocar/valve member being positioned, when in the flow position, so that
the tapered end of the member is retracted from the distal opening in the primary tube,
the valley in said body extends between said side opening and the first branching tube to enable communication therebetween, and
the third enlarged portion is withdrawn away from said second branching tube to enable communication between the distal opening of the primary tube and the second branching tube.

7. A catheter as in claim 6 wherein the tapered tip of the trocar/valve member is dimensioned to sealingly seat in the distal opening of the primary tube when said member is in the insert position, to thereby inhibit introduction of fluid through the distal opening while the catheter is being inserted into the body of a patient.

8. A catheter as in claim 7 wherein the exterior surface of the distal end of said primary tube and the surface of the tapered tip of said trocar/valve member are formed to present a generally smooth continuous exterior conical surface at the distal end when the trocar/valve member is in the insert position.

9. A catheter as in claim 6 wherein the end of said trocar/valve member opposite said one end protrudes out the proximal end of said primary tube, and wherein a flexible, tubular bellows means circumscribes and is sealingly attached to the proximal end of said primary tube and the end of said trocar/valve member which protrudes from the proximal end to thereby seal off the proximal end of said primary tube from the outside.

10. A catheter as in claim 6 wherein the cross section of the interior space of said primary tube is generally circular, wherein the cross section of said first enlarged portion of the trocar/valve member is generally semicircular to contact the interior wall of the top, bottom and said one side of the primary tube wherein the cross section of said second enlarged portion of the trocar/valve member is generally semi-circular to contact the interior wall of the top, bottom and said one side of the primary tube, and wherein the cross section of said third enlarged portion of the trocar/valve member is generally circular to substantially fill the interior space of the primary tube.

11. A catheter as in claim 6 wherein the elongate body of said trocar/valve member is formed, except for said enlarged portions and said tapered tip, as a partition extending between the interior walls of the primary tube to divide the interior of the tube into two lumens, each having a generally semi-circular cross section.

* * * * *